(12) United States Patent
Elgort et al.

(10) Patent No.: US 8,636,980 B2
(45) Date of Patent: Jan. 28, 2014

(54) MRI THERMOMETRY COMBINED WITH HYPERPOLARISATION DEVICE USING PHOTONS WITH ORBITAL ANGULAR MOMENTUM

(75) Inventors: Daniel R. Elgort, New York, NY (US); Lucian Remus Albu, Forest Hills, NY (US)

(73) Assignee: Koninklijke Philips N.V., Eindhoven (NL)

( * ) Notice: Subject to any disclaimer, the term of this patent is extended or adjusted under 35 U.S.C. 154(b) by 51 days.

(21) Appl. No.: 13/376,847

(22) PCT Filed: Jun. 14, 2010

(86) PCT No.: PCT/IB2010/052629
§ 371 (c)(1),
(2), (4) Date: Dec. 8, 2011

(87) PCT Pub. No.: WO2010/146517
PCT Pub. Date: Dec. 23, 2010

(65) Prior Publication Data
US 2012/0078082 A1    Mar. 29, 2012

Related U.S. Application Data

(60) Provisional application No. 61/218,461, filed on Jun. 19, 2009.

(51) Int. Cl.
*A61B 5/055*    (2006.01)
(52) U.S. Cl.
USPC ............................ 424/9.3; 424/9.37; 600/410
(58) Field of Classification Search
USPC ............. 600/407–436, 473–480; 424/9.3, 9.4
See application file for complete search history.

(56) References Cited

U.S. PATENT DOCUMENTS

| | | | |
|---|---|---|---|
| 4,586,511 A * | 5/1986 | Clark, Jr. | 424/9.37 |
| 5,357,959 A * | 10/1994 | Fishman | 600/420 |
| 5,545,396 A * | 8/1996 | Albert et al. | 424/9.3 |
| 5,642,625 A * | 7/1997 | Cates et al. | 62/55.5 |
| 5,785,953 A * | 7/1998 | Albert et al. | 424/9.3 |
| 6,051,208 A * | 4/2000 | Johnson et al. | 424/9.3 |
| 6,278,893 B1 * | 8/2001 | Ardenkj.ae butted.r-Larson et al. | 600/420 |

(Continued)

FOREIGN PATENT DOCUMENTS

WO    2009081360 A1    7/2009

OTHER PUBLICATIONS

Allen, L., et al.; Orbital angular momentum of light and the transformation of Laguerre-Gaussian laser modes; 1992; Physical Review A; 45(11)8185-8190.

(Continued)

*Primary Examiner* — Sanjay Cattungal

(57) ABSTRACT

A magnetic resonance examination system comprises an RF-system for inducing resonance in polarized dipoles and receiving magnetic resonance signals from an object to be examined. A thermometry module dervies a temperature distribution of the object to be examined from the magnetic resonance signals. The magnetic resonance examination system further comprises a photonic-based hyperpolarization device with a photonic source for emitting electromagnetic radiation, a moder converter, such as a phase hologram to impart orbital angular momentum to the electromagnetic radiation and via spatial filter to select from the phase hologram a diffracted photonic beam endowed with orbital angular momentum for polarizing the dipoles via transferred orbital angular momentum.

12 Claims, 2 Drawing Sheets

(56) References Cited

U.S. PATENT DOCUMENTS

| | | | |
|---|---|---|---|
| 6,426,058 B1 * | 7/2002 | Pines et al. | 424/9.3 |
| 6,453,188 B1 * | 9/2002 | Ardenkjaer-Larsen et al. | 600/420 |
| 6,818,202 B2 * | 11/2004 | Pines et al. | 424/9.3 |
| 7,576,538 B2 * | 8/2009 | Meersmann et al. | 324/309 |

OTHER PUBLICATIONS

De Zwart, J. A., et al.; On-Line Correction and Visualization of Motion During MRI-Controlled Hyperthermia; 2001; MRM; 45:128-137.

Elgort, D. R., et al.; Direct Optical Hyperpolarization of Liquids; 2008; Proc. Intl. Soc. Mag. Reson. Med.; 16:3200.

Franke-Arnold, S., et al.; Advances in optical angular momentum; 2008; Laser & Photonics Reviews; 2(4)299-313.

Hagen, G. M., et al.; Biological applications of an LCoS-Based Programmable Array Microscope (PAM); 2007; Proc. of Intl. Soc. for Optical Engineering; vol. 6441:64410S-1.

Salomir, R., et al.; Local Hyperthermia with MR-Guided Focused Ultrasound: Spiral Trajectory of the Focal Point Optimized for Temperature Uniformity in the Target Region; 2000; J. MRI; 12:571-583.

Wu, X., et al.; Optical Pumping and MRI of Hyperpolarized Spins; 2003; Biomedical Photonics Handbook; CRC Press; pp. 1-28.

\* cited by examiner

MRI THERMOMETRY COMBINED WITH HYPERPOLARISATION DEVICE USING PHOTONS WITH ORBITAL ANGULAR MOMENTUM

CROSS REFERENCE TO RELATED APPLICATIONS

This application claims the benefit of U.S. provisional application Ser. No. 61/218,461 filed Jun. 19, 2009, which is incorporated herein by reference.

FIELD OF THE INVENTION

The invention pertains to a magnetic resonance examination system provided with a photonic based hyperpolarisation device.

BACKGROUND OF THE INVENTION

Such a magnetic resonance examination system is described in the international application PCT/IB2008/055444. This magnetic resonance examination system comprises a hyperpolarisation device that is photonic based. In particular the hyperpolarisation device generates a photonic (e.g. light) beam that is endowed with orbital angular momentum. The orbital angular momentum of the light beam couples with (nuclear or molecular) dipoles (or spins) to generate (nuclear or molecular) polarisation. This polarisation is excited by RF-radiation and upon relaxation of the excitation, magnetic resonance signals are generated. From these magnetic resonance signals a magnetic resonance image is reconstructed. Because the polarisation is generated by the orbital angular momentum of the light beam, either no external magnetic field or only a weak magnetic field is needed to generate magnetic resonance signals with a relatively high signal-to-noise ratio. The known magnetic resonance examination system is able to image morphology of the object to be examined, notably of morphological images of the anatomy of a patient to be examined can be made.

SUMMARY OF THE INVENTION

An object of the invention is to provide a magnetic resonance examination system based on hyperpolarisation via orbital angular momentum that is able to measure temperature in a spatially resolved way. This object is achieved by the magnetic resonance examination system of the invention which comprises
- an RF-system for inducing resonance in polarised dipoles and receiving magnetic resonance signals from an object to be examined
- a thermometry module to derive a temperature distribution of the object to be examined from the magnetic resonance signals and the magnetic resonance examination system further comprising
  - a photonic-based hyperpolarisation device with
  - a photonic source for emitting electromagnetic radiation
  - a mode converter to impart orbital angular momentum to the electromagnetic radiation
  - a spatial filter to select from the phase hologram a diffracted photonic beam endowed with orbital angular momentum for polarising the dipoles via transferred orbital angular momentum.

The invention is based on the insight that the phase of the magnetic resonance signals is dependent of temperature. A further insight of the present invention is that also when magnetic resonance signals are generated by a photonic, that is an electromagnetic, notably optical, beam endowed with orbital angular momentum, these magnetic resonance signals contain local temperature information. When the magnetic resonance signals are spatially encoded, notably by way of read encoding and phase encoding, the phase of the magnetic resonance signals contains information on the local temperature. With the photonic, notably optical, hyperpolarisation approach, spatial encoding can also be accomplished by scanning the beam through the field of view. Thus, magnetic gradient fields for spatial encoding can optionally be dispensed with so that patient motion will not contribute to phase (leaving only the temperature dependent phase).

Electromagnetic (EM) radiation at any wavelength that is endowed with OAM will induce a nuclear polarization when it interacts with molecules. The photonic beam endowed with OAM is produced by a mode converter from the photonic beam of electromagnetic radiation from the photonic source. The mode converter for example includes a set of cylindrical lenses, optionally posed at different angels. Alternatively, the mode converter includes a phase hologram, for example in the form of a phase plate or a hologram plate. The phase hologram can also be formed by a computer generated hologram with a spatial modulator. A very practical embodiment of such a phase hologram is formed by a so-called LcoS (Liquid Crystal on Silicon) panel on which a hologram pattern is generated.

The photonic beam endowed with OAM can be an optical beam, i.e. having a wavelength in the range of visible radiation (e.g. between 380 nm and 780 nm). In particular optical radiation with a wavelength in the range from 400 nm (ultraviolet) to 1.3 µm (far infrared) can be employed. For wavelengths in the range from ultraviolet to far infrared, semiconductor lasers (e.g. based on GaN, GaAs or GaInP) can be employed as the source of electromagnetic radiation. The optical radiation interacts with electron orbitals in the molecules of the material (e.g. tissue) to be examined and causes electron spin orientation. The orbital angular momentum of the photonic beam couples with molecular rotational states and orientates the molecules. Accordingly, the hyperpolarisation is enhanced. Subsequently, by way of hyperfine interactions the electron spin is transferred to the nuclei of the material. Finally , the hyperpolarised nuclei are excited ('flipped') by an RF-pulse and upon return (by precession) to the preferred orientation, magnetic resonance signals are generated. The wavelength is chosen on the basis of a suitable compromise between the level of absorption required to excite the electron orbitals versus the required penetration depth into the material, e.g. tissue, to be examined.

It is found that the polarisaation degree is highest in the beam focal spot and also that the polarisation degree increases with decreasing of the beam width. That is, the smaller the beam width the better, but minimum beam width is not necessary to achieve a high degree (up to more than 10-20% or more) polarisation. Finally, the theory indicates that the probability of polarization is proportional to absolute beam width.

The focal spot of the beam can be translated both laterally and along the depth position in a number of ways. Mirrors/focusing elements can be rotated or physically translated. The radius of curvature of a focusing element can be altered, such that the depth of focus is moved to a different depth, a beam splitter or mirror can send the photonic beam along alternate photonic paths that each have different focusing depths, or the properties of the phase hologram can be altered (e.g. by using a computer controlled LCoS panel or using multiple phase plates) such that the OAM endowed beam will focus at different depths. When designing a system that focuses at different depths, it may be important to ensure that the wavelength(s) in the light source are able to penetrate to the desired range of depths.

The photonic beam endowed with OAM can be an optical beam, i.e. having a wavelength in the range of visible radiation (e.g. between 380 nm and 780 nm). Alternatively also other wavelength ranges such as ultraviolet (below 400 nm) or infrared (above 780 nm) can be employed. All these examples are encompassed by the term photonic. Other options are soft x-rays or microwave radiation which has a wavelength in the range 0.8 µto 1 m The electromagnetic source accordingly emits photonic radiation with a wavelength in any of these ranges.

However, the rate at which the polarization evolves and the ultimate equilibrium polarization may be higher or lower depending on the EM wavelength and amount of OAM. Experiments and theory indicate that the OAM induced polarization is more effective (i.e. the probability of OAM transfer from photon to molecule increases) when the EM beam radius is small. Since shorter wavelengths can be focused to smaller beam radii, they have the potential to provide be more effective at achieving high degrees of nuclear polarization. Choosing wavelengths that interact more strongly with the specific molecular targets will also improve the efficiency of OAM transfer and therefore nuclear polarization; however, with respect to this criteria, it is advantageous to choose wavelengths that do not interact strongly with molecules in the target tissue if, for example, it is desirable to trade-off rate of hyperpolarisation with depth penetration.

The generation of temperature maps from magnetic resonance signals is discussed per se in 'Local hyperthermia with MR-guided focused ultrasound: spiral trajectory for the focal point optimized for temperature uniformity in the target region' in J. Magn. Res. Im. 12(2000)571-583. by R. Salomir et al., where the magnetic resonance signals are generated by a magnetic resonance examination system that employs a strong magnetic field for generating the polarisation of the nuclei or molecules.

The temperature measurement can be made by precision measurements of frequency (or changes in frequency) in addition to phase-based temperature measurements. The frequency-based temperature measurements are implemented for example on a point-by-point basis, which this approach lends itself to because each point within the FOV can be hyperpolarized and interrogated separately (i.e. the FOV can be sampled directly in the "image domain" instead of the Fourier domain).

Because only a weak external magnetic field or no external magnetic field at all is required to generate the thermometric information to guide the high-intensity ultrasound beam several advantages are achieved. Because there is no need for a high field magnetic resonance examination system with a narrow bore, but e.g. an open magnetic resonance examination system with low field, such as a field strength of 1T or even less, e.g. 0.23T access to the patient is easier. If no external magnetic field is required, the photonic-based hyperpolarisation device can be designed as a hand held device and patient access is greatly enhanced. If no external magnetic field is applied, then there are no restriction concerning the use of metallic instruments. Further, the magnetic resonance examination system of the invention is relatively inexpensive because no expensive main magnet system is required.

These and other aspects of the invention will be further elaborated with reference to the embodiments defined in the dependent Claims.

An embodiment of the magnetic resonance examination system of the invention is provided with a motion detection module. Accurate results are obtained when a motion correction is applied and phase contribution due to motion are separated from phase contributions due to temperature changes. The motion correction can be derived from the magnetic resonance signals, notably by redundant magnetic resonance signals from the central portion of k-space. To this end, acquisition strategies that oversample the centre of k-space are suitable, such as radial, spiral or PROPELLER acquisitions. Alternatively, the motion detection module may be configured to apply magnetic resonance navigators from which motion in or of the patient to be examined is derived. A motion detection module is provided to derive the motion correction and apply motion compensation to the magnetic resonance signals. The motion corrected magnetic resonance signals are applied to the thermometry module which derives local temperature distribution of a target zone. Alternatively, the motion compensation module can be configured or programmed in software to derive separate the contribution to the phase of magnetic resonance signals due to motion and compute the contribution of the phase due to temperature changes. The detected motion is applied to the thermometry module to separate phase contributions to the magnetic resonance signals from motion and temperature, respectively.

The invention further pertains to a therapeutic assembly which comprises a therapy module, a magnetic resonance signals and a therapy controller which controls the therapy module on the basis of the temperature distribution formed by the thermometry module of the magnetic resonance examination system. According to this aspect of the invention, the thermometry module is employed for guiding a therapy module. The therapy module functions to deposit energy, preferably locally in a target zone in the patient's anatomy. Thus, locally the temperature is elevated which causes local material changes, e.g. necrosis or cell death, in the tissue. On the basis of the temperature distribution that is obtained by the thermometry module, the therapy module is controlled so as to accurately deposit energy in the target zone, while avoiding healthy tissue next to the target zone. For example, the energy may be deposited in a tumour, to cause the tumour (cancerous) tissue to be necrotic and be removed. For example, a high-intensity focused ultrasound beam or RF or laser ablation may be employed to deposit energy and generate locally elevated temperature. For example, in cardiac applications RF-ablation or laser ablation is employed to treat cardiac arrhythmia by locally changing the electrical conductivity properties of the patient's myocardium. Alternatively, hyperthermia treatment can be applied by locally lowering temperature.

As to the polarisation of nuclei or molecules (i.e. nuclear or molecular dipole moments) the present invention has the following aspects. In accordance with one aspect, a magnetic resonance system is provided. A light-based hyperpolarisation device polarizes a selected dipole via transferred orbital angular momentum. An RF system induces resonance in the polarized dipoles and receives resonance signals.

In accordance with another aspect, a surface probe is provided. A light output unit directs light to penetrate tissue of a patient. A light-based hyperpolarisation system imparts orbital angular momentum to generated light. The light to which orbital angular momentum has been imparted is discharged through the light output unit to polarize selected dipoles in the patient.

These and other aspects of the invention will be elucidated with reference to the embodiments described hereinafter and with reference to the accompanying drawing wherein

DETAILED DESCRIPTION OF THE EMBODIMENTS

Figure 1:
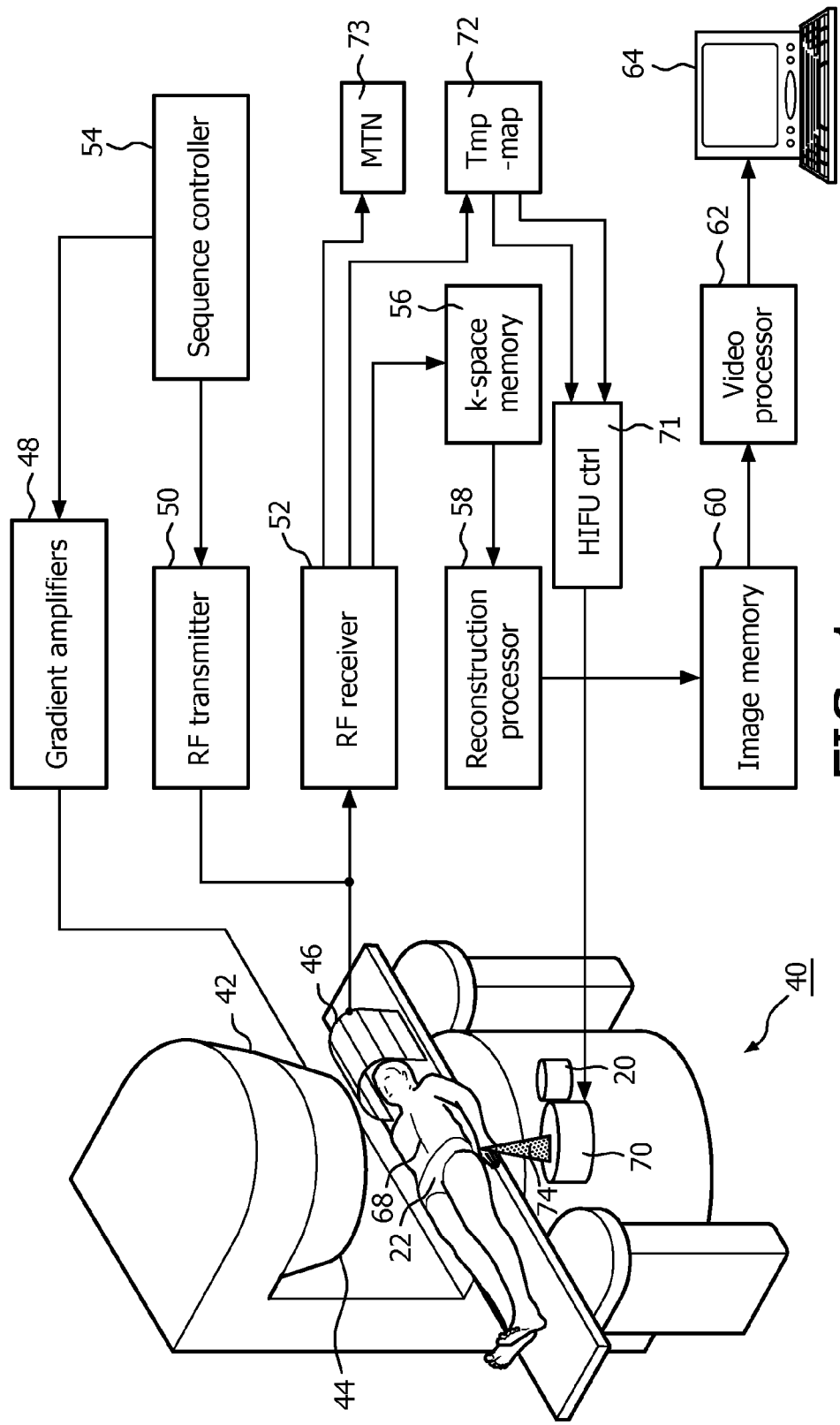
FIG. 1 is a diagrammatic illustration of a magnetic resonance imaging apparatus in accordance with the present application and FIG. 2 shows an exemplary arrangement of optical elements is shown for endowing light with OAM.
Figure 2:
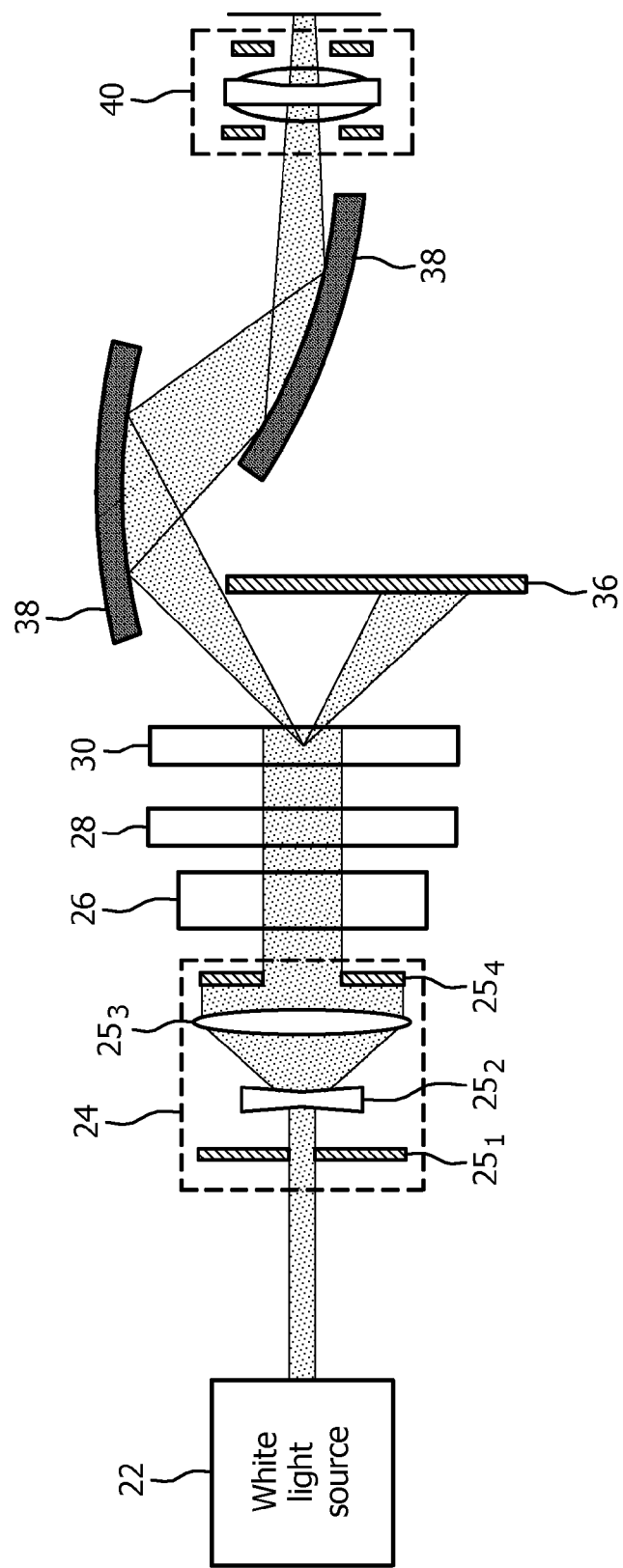

In one embodiment, as shown in FIG. 1, the OAM-endowed light-emitting device as described above can be used in conjunction with a magnetic resonance scanner 40. Details of the OAM light endowing device 20 are shown in FIG. 2.

The magnetic resonance scanner 40 can be an open field system (open MRI system) that includes a vertical main magnet assembly 42. The main magnet assembly 42 produces a substantially constant main magnetic field oriented along a vertical axis of an imaging region. Although a vertical main magnet assembly 42 is illustrated, it is to be understood that other magnet arrangements, such as cylindrical, and other configurations are also contemplated.

A gradient coil assembly 44 produces magnetic field gradients in the imaging region for spatially encoding the main magnetic field. Preferably, the magnetic field gradient coil assembly 44 includes coil segments configured to produce magnetic field gradient pulses in three orthogonal directions, typically longitudinal or z, transverse or x, and vertical or y directions. Both the main magnet assembly 42 and the gradient field assembly 44 in some embodiments are used along with photonic polarization.

A radio frequency coil assembly 46 (illustrated as a head coil, although surface and whole body coils are also contemplated) generates radio frequency pulses for exciting resonance in dipoles of the subject. The radio frequency coil assembly 46 also serves to detect resonance signals emanating from the imaging region. The radio frequency coil assembly 46 can be used to supplement photonic perturbation of previously established polarization.

Gradient pulse amplifiers 48 deliver controlled electrical currents to the magnetic field gradient assembly 44 to produce selected magnetic field gradients. A radio frequency transmitter 50, preferably digital, applies radio frequency pulses or pulse packets to the radio frequency coil assembly 46 to excite selected resonance. A radio frequency receiver 52 is coupled to the coil assembly 46 or separate receive coils to receive and demodulate the induced resonance signals.

To acquire resonance imaging data of a subject 22, e.g. a patient to be examined or treated by the high-intensity focused ultrasound, the subject is placed inside the imaging region. A sequence controller 54 communicates with the gradient amplifiers 48 and the radio frequency transmitter 50 to supplement the photonic manipulation of the region of interest. The sequence controller 54 may, for example, produce selected repeated echo steady-state, or other resonance sequences, spatially encode such resonances, selectively manipulate or spoil resonances, or otherwise generate selected magnetic resonance signals characteristic of the subject. The generated resonance signals are detected by the RF coil assembly 46, communicated to the radio frequency receiver 52, demodulated and stored in a k-space memory 56. The imaging data is reconstructed by a reconstruction processor 58 to produce one or more image representations that are stored in an image memory 60. In one suitable embodiment, the reconstruction processor 58 performs an inverse Fourier transform reconstruction.

The resultant image representation(s) is processed by a video processor 62 and displayed on a user interface 64 equipped with a human readable display. The interface 64 is preferably a personal computer or workstation. Rather than producing a video image, the image representation can be processed by a printer driver and printed, transmitted over a computer network or the Internet, or the like. Preferably, the user interface 64 also allows a radiologist or other operator to communicate with the sequence controller 54 to select magnetic resonance imaging sequences, modify imaging sequences, execute imaging sequences, and so forth.

Moreover, a high-intensity focused ultrasound (HIFU) system 70 is incorporated in the magnetic resonance examination system of the invention. The HIFU system 70 is configured to emit a focused ultrasound beam 74 onto a target zone within the patient 22 to be examined. To that end, the HIFU system is fitted with a transducer array that is controlled by a HIFU controller 71. The high-intensity focused ultrasound beam creates an elevated temperature in the target zone onto which it is focused. The elevated temperature causes cell-death (necrosis) in the target zone. Thus, e.g. cancerous tissue is rendered necrotic so that the tumour does not spread and ultimate tumour tissue is eliminated. The high-intensity focused ultrasound beam is accurately controlled so as to avoid that health tissue next to the target zone is damaged. According to the invention, the focused ultrasound beam is controlled on the basis of the temperature distribution of the target zone. The temperature distribution is derived from the magnetic resonance signals that are acquired by the RF receiver. The temperature module 72 receives the magnetic resonance signals and derives the local temperature from the phase information in the magnetic resonance signals. Notably, the local temperature distribution is collected in the form of a so-called temperature map which represents the local temperature as s function of position (in the magnetic resonance image or equivalently in the patient's anatomy). The temperature map is applied as an input to the HIFU controller which then on the basis of the current temperature map controls the high-intensity focused ultrasound beam direction and/or intensity so that the predetermined temperature distribution within margins is achieved. The motion correction unit 73 is arranged to receive magnetic resonance signals from the RF receiver. The magnetic resonance signals applied to the motion correction unit 73 are for example magnetic resonance signals from the centre region of k-space with high redundancy, e.g. by way of a PROPELLOR acquisition or in the form of MR navigator signals, e.g. non-phase-encoded signals from small region in which there is a clear anatomical transition. In particular, good results are achieved in practice when applied to thermography (to control HIFU)of mobile tissues like liver tumours and kidney tumours.

With reference now to FIG. 2, an exemplary arrangement of optical elements is shown for endowing light with OAM. It is to be understood that any electromagnetic radiation can be endowed with OAM, not necessarily only visible light. The described embodiment uses visible light, which interacts with the molecules of interest, and has no damaging effect on living tissue. Light/radiation above or below the visible spectrum, however, is also contemplated. A white light source 22 produces visible white light that is sent to a beam expander 24. In alternate embodiments, the frequency and coherence of the light source can be used to manipulate the signal if chosen carefully, but such precision is not essential. The beam expander includes an entrance collimator 251 for collimating the emitted light into a narrow beam, a concave or dispersing lens 252, a refocusing lens 253, and an exit collimator 254 through which the least dispersed frequencies of light are emitted. In one embodiment, the exit collimator 254 narrows the beam to a 1 mm beam.

After the beam expander 24, the light beam is circularly polarized by a linear polarizer 26 followed by a quarter wave plate 28. The linear polarizer 26 takes unpolarized light and gives it a single linear polarization. The quarter wave plate 28 shifts the phase of the linearly polarized light by ¼ wavelength, circularly polarizing it. Using circularly polarized light is not essential, but it has the added advantage of polarizing electrons.

Next, the circularly polarized light is passed through a phase hologram 30. The phase hologram 30 imparts OAM and spin to an incident beam. The value "1" of the OAM is a parameter dependent on the phase hologram 30. In one embodiment, an OAM value 1=40 is imparted to the incident light, although higher values of 1 are theoretically possible. The phase hologram 30 is a computer generated element and is physically embodied in a spatial light modulator, such as a liquid crystal on silicon (LCoS) panel, 1280×720 pixels, 20×20 μm2, with a 1 μm cell gap. Alternately, the phase hologram 30 could be embodied in other optics, such as combinations of cylindrical lenses or wave plates. The spatial light modulator has the added advantage of being changeable, even during a scan, with a simple command to the LCoS panel.

Not all of the light that passes through the holographic plate 30 is imparted with OAM and spin. With reference now to FIG. 4, a projection of the light that passes through the holographic plate 30 is depicted. Generally, when electromagnetic waves with the same phase pass through an aperture, it is diffracted into a pattern of concentric circles some distance away from the aperture (Airy pattern). The bright spot (Airy disk) 32 in the middle represents the 0th order diffraction, in this case, that is light with no OAM. The circles 34 adjacent the bright spot 32 represent diffracted beams of different harmonics that carry OAM. This distribution results because the probability of OAM interaction with molecules falls to zero at points far from the center of the light beam or in the center of the light beam. The greatest chance for interaction occurs on a radius corresponding to the maximum field distribution, that is, for circles close to the Airy disk. Therefore, the maximum probability of OAM interaction is obtained with a light beam with a radius as close as possible to the Airy disk radius.

With reference to FIG. 2, a spatial filter 36 is placed after the holographic plate to selectively pass only light with OAM and spin. An example of such a filter is shown in FIG. 5. The 0th order spot 32 always appears in a predictable spot, and thus can be blocked. As shown, the filter 36 allows light with OAM to pass. Note that the filter 36 also blocks the circles that occur below and to the right of the bright spot 32. Since OAM of the system is conserved, this light has OAM that is equal and opposite to the OAM of the light that the filter 36 allows to pass. It would be counterproductive to let all of the light pass, because the net OAM transferred to the target molecule would be zero. Thus, the filter 36 only allows light having OAM of one polarity to pass.

With continuing reference to FIG. 2, the diffracted beams carrying OAM are collected using concave mirrors 38 and focused to the region of interest with a fast microscope objective lens 40. The mirrors 38 may not be necessary if coherent light were being used. A faster lens (having a high f-number) is desirable to satisfy the condition of a beam waist as close as possible to the size of the Airy disk. In alternate embodiments, the lens 40 may be replaced or supplemented with an alternative light guide or fiber optics.

The invention claimed is:

1. A magnetic resonance examination system comprising:
an RF-system for inducing resonance in polarised dipoles and receiving magnetic resonance signals from an object to be examined;
a thermometry module to derive a temperature distribution of the object to be examined from the magnetic resonance signals; and
a photonic-based hyperpolarisation device comprising,
a photonic source for emitting electromagnetic radiation,
a mode converter to impart orbital angular momentum to the electromagnetic radiation, and
a spatial filter to select from the phase hologram a diffracted photonic beam endowed with orbital angular momentum for polarizing the dipoles via transferred orbital angular momentum.

2. The magnetic resonance examination system as claimed in claim 1, including a motion correction unit to detect motion of the object to be examined and apply a motion correction to the thermometry module.

3. The magnetic resonance examination system according to claim 2, wherein the motion correction unit is configured to derive a phase contribution of the magnetic resonance signals due to motion and a phase contribution of the magnetic resonance signals due to temperature changes.

4. A therapy assembly comprising:
a therapy module to locally deposit energy in a subject;
the magnetic resonance examination system of claim 1; and
a therapy controller to control the therapy module on the basis of the temperature distribution provided by the thermometry module.

5. The magnetic resonance examination system according to claim 1, further comprising:
a sequence controller to acquire resonance imaging data of a subject, wherein the sequence controller produces resonance sequences, spatially encodes the resonance sequences, and generates selected magnetic resonance signals characteristic of the subject.

6. The magnetic resonance examination system according to claim 5, further comprising:
a reconstruction processor to reconstruct the resonance imaging data to produce reconstructed image representations that are stored in an image memory.

7. The magnetic resonance examination system according to claim 6, further comprising:
a reconstruction processor that performs an inverse Fourier transform reconstruction to reconstruct the resonance imaging data to produce reconstructed image representations that are stored in an image memory.

8. The magnetic resonance examination system according to claim 6, further comprising:
a video processor that processes and displays the reconstructed image representations on a user interface.

9. The magnetic resonance examination system according to claim 1, wherein the mode converter includes a set of collimators with a dispersing lens and a refocusing lens to emit least dispersed frequencies of light.

10. The magnetic resonance examination system according to claim 9, wherein the emitted light is circularly polarized by a linear polarizer followed by a quarter wave plate.

11. The magnetic resonance examination system according to claim 10, wherein the circularly polarized light is imparted with orbital angular momentum by passing through a phase hologram.

12. The magnetic resonance examination system according to claim 11, wherein the circularly polarized light imparted with orbital angular momentum is in the range of visible radiation, ultraviolet radiation, infrared radiation, or soft x-ray radiation.

* * * * *